United States Patent [19]

Bachman

[11] 4,111,925

[45] Sep. 5, 1978

[54] HYDROLYSIS OF ESTERS OF α-L-ASPARTYL-L-PHENYLALANINE

[75] Inventor: Gerald L. Bachman, Kirkwood, Mo.

[73] Assignee: Monsanto Company, St. Louis, Mo.

[21] Appl. No.: 842,421

[22] Filed: Oct. 14, 1977

[51] Int. Cl.$^2$ ............................................. C07C 103/52
[52] U.S. Cl. ............................................... 260/112.5 R
[58] Field of Search ................................. 260/112.5 R

[56] References Cited

U.S. PATENT DOCUMENTS

| | | | |
|---|---|---|---|
| 3,808,190 | 4/1974 | Dahlmans et al. | 260/112.5 R |
| 3,833,554 | 9/1974 | Ariyoshi et al. | 260/112.5 R |

*Primary Examiner*—Delbert R. Phillips
*Attorney, Agent, or Firm*—Robert E. Wexler; Edward P. Grattan; Stanley M. Tarter

[57] ABSTRACT

A process which comprises contacting alkyl esters of α-L-aspartyl-L-phenylalanine with an aqueous solution containing barium ions, at a reaction pH greater than 7, to form α-L-aspartyl-L-phenylalanine.

13 Claims, No Drawings

HYDROLYSIS OF ESTERS OF α-L-ASPARTYL-L-PHENYLALANINE

BACKGROUND OF THE INVENTION

1. Field of the Invention

This invention relates to a process for obtaining α-L-aspartyl-L-phenylalanine, in particular, by hydrolyzing alkyl esters of α-L-aspartyl-L-phenylalanine. Certain alkyl esters of α-L-aspartyl-L-phenylalanine are well known for their usefulness as sweetening agents.

2. Description of Prior Art

α-L-aspartyl-L-phenylalanine is a precursor material in a process for the preparation of certain alkyl esters of α-L-aspartyl-L-phenylalanine which is described in U.S. Pat. No. 3,933,781 issued to Bachman, Oftedahl and Vineyard on Jan. 20, 1976. Copending Application Ser. No. 754,297 filed Dec. 27, 1976 also describes a process to prepare certain alkyl esters of α-L-aspartyl-L-phenylalanine in which α-L-aspartyl-L-phenylalanine is involved in forming the ester.

In the process of U.S. Pat. No. 3,933,781 α-L-aspartyl-L-phenylalanine is subjected to esterification with an alkanol to form the desired ester according to the following reaction:

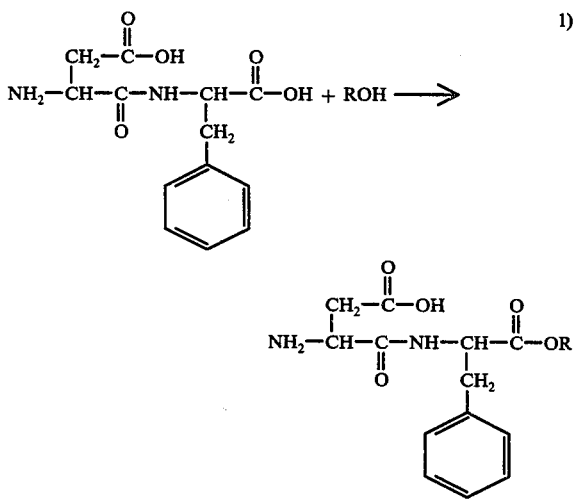

When R in the above reaction is methyl the product formed is α-L-aspartyl-L-phenylalanine methyl ester (hereinafter referred to as α-APM) which is well known for its usefulness as a sweetening agent. For convenience, α-APM will hereinafter be used as an example of the type of ester which is formed in reaction 1) above. It is to be understood that α-APM is used for illustrative purposes and is not to be construed as a limitation of this invention.

To obtain α-APM in substantially pure form, various separation and purification steps are described in U.S. Pat. No. 3,933,781. For instance, after α-L-aspartyl-L-phenylalanine undergoes esterification according to reaction 1) it is usually desirable to separate the α-APM from the following undesired by-products which are also produced during the esterification reaction:

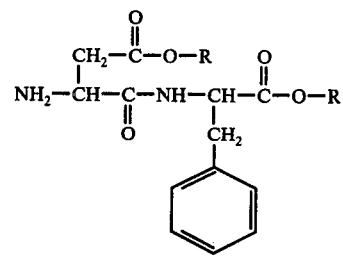

(hereinafter referred to as the "diester") and

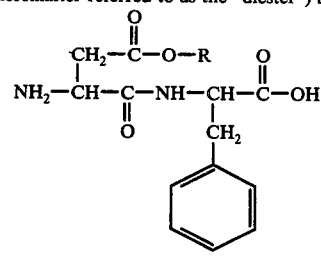

(hereinafter referred to as the "aspartyl ester"), R in the above structures being methyl when preparing α-APM.

The term "alkyl esters of α-L-aspartyl-L-phenylalanine" when used herein encompasses the aforementioned several forms of esters which are formed during the esterification of α-L-aspartyl-L-phenylalanine. Specifically, the term encompasses the desired ester form shown in reaction 1), diester and aspartyl ester.

The separation and purification steps to obtain α-APM in substantially pure form are difficult due to the similarity of materials present. Complete separation is often not possible, resulting in incomplete recovery of the α-APM during these separation and purification steps.

The production of undesired esters and incomplete recovery of the α-APM in separation and purification steps result in lower overall yields in a process to produce α-APM. It is therefore desirable to provide efficacious recovery methods to improve the economics of the process.

It is an object of this invention to provide a method for obtaining α-L-aspartyl-L-phenylalanine from alkyl esters of α-L-aspartyl-L-phenylalanine. The α-L-aspartyl-L-phenylalanine could then be recycled to produce α-APM according to reaction 1). The advantages of reduced waste and yield improvement are apparent to one skilled in the art.

Further objects, aspects and advantages of this invention will be apparent from the description and claims which follow.

SUMMARY OF THE INVENTION

In accordance with this invention alkyl esters of α-L-aspartyl-L-phenylalanine are hydrolyzed to produce α-L-aspartyl-L-phenylalanine by contacting the esters with an aqueous solution containing barium ions at a reaction pH greater than 7.

The hydrolysis is selective in that the alkyl esters of α-L-aspartyl-L-phenylalanine are converted to α-L-aspartyl-L-phenylalanine in very high yields and other products which would be expected to result from hydrolysis are avoided.

DESCRIPTION OF THE PREFERRED EMBODIMENTS

Several results are possible when alkyl esters of α-L-aspartyl-L-phenylalanine are subjected to hydrolysis. For instance, the reaction to hydrolyze α-APM may result in one or more of the following reactions:

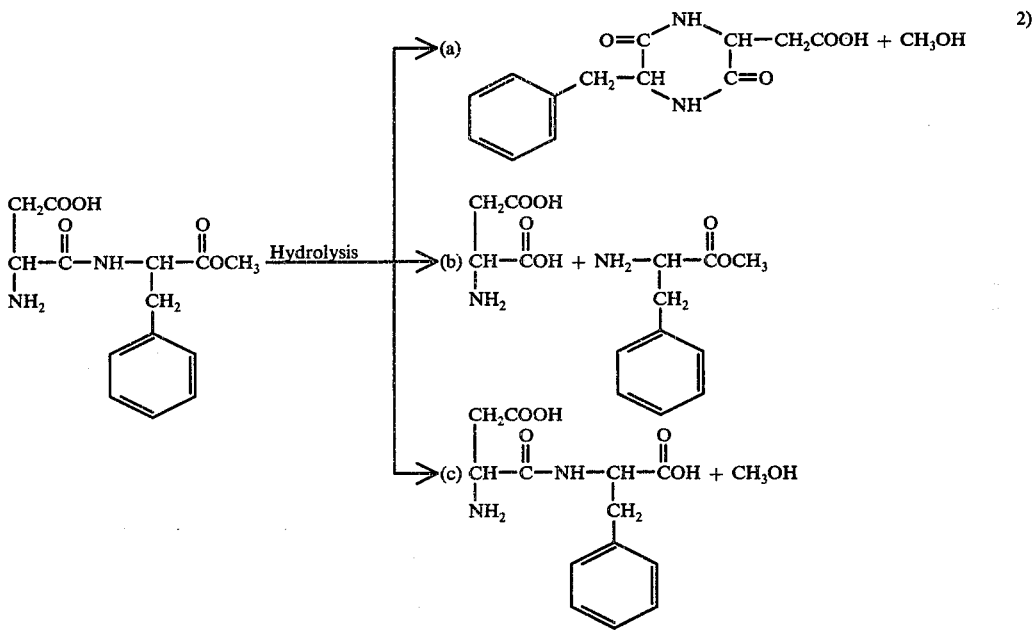

Reaction (a) represents the formation of a substituted diketopiperazine. Reaction (b) represents cleavage of the dipeptide bond of the α-L-aspartyl-L-phenylalanine ester to form L-aspartic acid and an alkyl ester of phenylalanine. The alkyl ester of phenylalanine formed in reaction (b) can be further hydrolyzed to form L-phenylalanine. According to reaction (c), α-L-aspartyl-L-phenylalanine is formed.

Hydrolysis of the diester and aspartyl ester can likewise produce various products proceeding in general according to the above reactions. In the hydrolysis of the diester there is the additional possibility of a monoester being produced if only one ester site is hydrolyzed.

According to the present invention, a process is provided to selectively produce α-L-aspartyl-L-phenylalanine in the hydrolysis of alkyl esters of α-L-aspartyl-L-phenylalanine. Hydrolysis proceeds substantially according to reaction (c), and reactions (a) and (b) are essentially avoided. Such results are unexpected and could not be predicted by one skilled in the art. Furthermore, such results are desirable, for example in the production of α-APM substantially according to the U.S. Pat. No. 3,933,781, since the α-L-aspartyl-L-phenylalanine can be readily recycled and re-esterified to realize economically valuable yield gains.

Hydrolysis of alkyl esters of α-L-aspartyl-L-phenylalanine by the process of this invention produces major amounts of α-L-aspartyl-L-phenylalanine. Only minor amounts of a substituted diketopiperazine have been detected in the product after hydrolysis according to this invention, and there has been essentially no indication of cleavage of the dipeptide bond. Avoiding the production of undesired products reduces difficult and costly separation requirements which would be necessary, for example, to obtain α-L-aspartyl-L-phenylalanine in a form suitable for recycle in a process to prepare α-APM.

The hydrolysis has been found to be efficacious with all ester forms of α-L-aspartyl-L-phenylalanine, that is, the ester form shown in reaction 1), the diester and the aspartyl ester. The hydrolysis can be carried out on one form or a mixture of various forms of esters. It is preferred that the alkyl group of said esters be a lower alkyl group. More preferred are the esters wherein the alkyl group contains from 1 to 3 carbon atoms. Still more preferred are the methyl esters.

It is recognized that the esters may exist as an acid salt, due, for example, to the nature of the process for the production of α-APM. Hydrolysis of the esters, nonetheless, can proceed according to the present invention if the acid salt is neutralized by means well-known in the art before or during the hydrolysis process.

The esters to be recovered by use of this invention may be contained in the various process side streams which result, for example, from purification and separation steps in the process of U.S. Pat. No. 3,933,781. Various esters of α-L-aspartyl-L-phenylalanine are normally present in these process streams. It has been discovered that the hydrolysis process described herein can be carried out directly on these process streams or combinations thereof, without isolation of the esters. However, depending on the materials present in the reaction mass, the recovery of α-L-aspartyl-L-phenylalanine using the hydrolysis procedure of this invention may be affected due to solubility or other causes.

Since the process is a hydrolysis process it is essential that the reaction be carried out in the presence of an aqueous solution. The method for introducing the water into solution is not critical as long as proper proportions are maintained.

A mole of water is required for each mole of dipeptide monoester to be hydrolyzed. In the case of a dipeptide diester, two moles of water per mole of dipeptide diester are required for complete hydrolysis. The mole ratio of water to dipeptide ester is significant only in determining the amount of ester which will be hydrolyzed. An excess of water is not detrimental to the reaction.

The solvent utilized in this reaction is water or a mixture of water and an organic solvent provided that the reactants are soluble in the mixture and the organic solvent does not interfere with the desired reaction. It is preferred to use water as the solvent.

It has surprisingly been found that the presence of barium ions in an aqueous solution causes selective hydrolysis of alkyl esters of α-L-aspartyl-L-phenylalanine to form α-L-aspartyl-L-phenylalanine when the solution is contacted with the esters at a reaction pH greater than 7. Other methods of hydrolysis were found to form substantial amounts of a substituted diketopiperazine or to cause substantial cleavage of the dipeptide bond of the alkyl ester of α-L-aspartyl-L-phenylalanine.

Various methods are available for obtaining an aqueous solution containing barium ions. For example, such a solution can be formed by bringing together barium, barium oxide or barium hydroxide and water. The use of barium oxide or barium hydroxide is preferred. It is recognized that barium hydroxide may be in the form of a hydrate. Other materials which may be used as a source of barium ions will be apparent to those skilled in the art.

It has been determined that one mole of barium ions is required for each mole of dipeptide ester to be hydrolyzed. The number of ester sites on the dipeptide does not affect the required moles of barium ions. Therefore, the same number of moles are required for the monoester and diester of the dipeptide. Partial hydrolysis will result if the moles of dipeptide ester exceed the moles of barium ions present. An excess of barium ions is not known to be detrimental to the reaction but large excesses may result in undesirable side reactions.

Although it is preferred to add the barium-containing substance to water, and then add the ester, it is possible to vary the sequence of addition of materials. For example, it is possible to introduce the barium source to a mixture of the ester in water. Other variations will be apparent to those skilled in the art. The particular sequence of addition of materials is not critical.

The reaction must be carried out at a pH greater than 7. This pH, herein referred to as "reaction pH", is that of the reaction mass which comprises the aqueous solution containing barium ions and the ester which are brought together in the process of this invention. As the reaction pH is increased the rate of hydrolysis is increased. Particularly preferred is a reaction pH greater than about 10. Most preferred is a reaction pH from about 10.5 to about 13.5. It is preferred to use barium oxide or barium hydroxide to adjust pH. However, other bases, such as sodium hydroxide or potassium hydroxide, can also be used.

Temperature and pressure of the reaction are not critical. The reaction proceeds rapidly at room temperature and atmospheric pressure. A temperature range of 0° C. to 100° C. can be utilized. However, at higher temperatures secondary reactions such as racemization, may occur. Therefore, it is preferred to carry out the reaction at a temperature below about 50° C. More preferred is a temperature from about 20° C. to about 40° C.

The reaction time is not critical. The reaction is essentially instantaneous at ambient conditions at a reaction pH greater than about 10. Illustrative of a method for obtaining adequate contact of materials is holding the solution at reaction conditions for about 15 minutes to about 1 hour with continuous stirring during that time.

The α-L-aspartyl-L-phenylalanine produced can be recovered from the reaction mass by precipitation and liquid/solid separation. Such precipitation can, for instance, be produced by adjusting the pH of the mixture to acid conditions and cooling the mixture to below about 10° C.

The following examples are given to illustrate the invention in detail. It is to be understood that the specific details given in the examples are not to be construed as limiting the scope of the invention.

The materials and procedures utilized in the thin layer chromatography (TLC) analyses in the examples are as follows:

A. Plate

Silica Gel F on glass plate supplied by Brinkman Instrument Inc., Westbury, N.Y. 11590.

B. Solvent Systems

| 1. | chloroform | 64% (by volume) |
|---|---|---|
| | methanol | 30% (by volume) |
| | acetic acid | 2% (by volume) |
| | distilled water | 4% (by volume) |
| 2. | n-propanol | 70% (by volume) |
| | distilled water | 10% (by volume) |
| | methanol | 10% (by volume) |
| | formic acid | 10% (by volume) |

C. Detection Spray Solutions 1. 0.3 g. of ninhydrin dissolved in a mixture of 100 ml. of n-butanol and 3 ml. of glacial acetic acid.

2. 1 g. of potassium iodide and 1 g. of soluble starch dissolved in 100 ml. of distilled water.

D. Procedures

After spotting and development in the appropriate solvent system the plate was dried for 30 min.

Ninhydrin spray — The plate was sprayed and held in a 100° C. oven for 15 min.

Starch-iodide spray — The plate was placed in a chamber saturated with t-butyl hypochlorite vapor for 15 min., air dried for 30 min. then sprayed with freshly prepared starch-iodide solution.

The following examples were all carried out at atmospheric pressure. Unless otherwise specified, all percentages in the examples are by weight.

EXAMPLE I

To a 40° C. solution of 287.6 g. (1.875 moles) of BaO in 2000 ml. of water was added 500 g. (1.7 moles) of α-APM over 20 minutes. The mixture was stirred 1 hour at ambient temperature and filtered to clarify. The cake was washed with 230 ml. of 25° C. water. The combined filtrate and wash was cooled to 0° C. (pH = 13.3) and 1170 g. of acetic acid was added over 4⅓ hours with external cooling. After stirring for 0.5 hours (Temperature = −3° C., pH = 3.7) the pH was adjusted to 3.0 with 203.2 g. of 37 percent HCl. The batch was stirred for 0.5 hour and the precipitate was removed by suction filtration. The cake was washed with two 500 ml. portions of 5° C. water and dried at 55°–60° C. in a vacuum oven. The yield of α-L-aspartyl-L-phenylalanine was 397 g. (83.4 percent of theory). TLC analysis indicated 97.5 percent α-L-aspartyl-L-phenylalanine, 1.45 percent NaCl, less than 1 percent substituted diketopiperazine and no detectable α-APM, L-aspartic acid or L-phenylalanine.

EXAMPLE II

α-APM was produced substantially according to U.S. Pat. No. 3,933,781. The liquors and wash waters resulting from the various separation and purification steps were combined. The combined reaction mass totaled 1238 g. and contained α-L-aspartyl-L-phenylalanine, α-APM, aspartyl ester and diester (total of 0.3 mole of α-L-aspartyl-L-phenylalanine equivalent for all of these ester forms). The mixture was concentrated by distillation of water (45°–50° C. and 40–50 mm. Hg) to 817 g. The pH of the concentrate (30° C.) was adjusted to 3.0 with 40 g. of 50 percent NaOH. The pH was further adjusted to 11.7 (40° C.) with 89 g. (0.58 mole) of BaO. The mixture was stirred for 0.5 hour at 40° C., then cooled to 5° C. While maintaining the temperature at 5°–10° C., the pH was adjusted to 2.85 with 107 g. of 37 percent HCl. The batch was stirred at 0°–5° C. for 1 hour. The solid precipitate was separated by centrifugation and was washed with 330 ml. of cold water. The cake was dried at 60° C. and 150 mm. The yield was 43.5 g. (51.7 percent of theory) of α-L-aspartyl-L-phenylalanine which was shown to be 97 percent pure by TLC.

EXAMPLE III

To a stirred 30° C. slurry of 5 g. (approximately 0.017 mole) of crude α-APM (90-95 percent α-APM, 5–10 percent of α-L-aspartyl-L-phenylalanine, 0.5–1.5 percent substituted diketopiperazine) in 34 ml. of distilled water was added portionwise over 5 minutes 2.6 g. (0.017 mole) of BaO. The resulting reaction mass, which had an alkaline pH, was stirred for 2 hours at 30° C. The solution was analyzed by TLC and no residual α-APM was detected. The TLC analysis showed only α-L-aspartyl-L-phenylalanine (97.5–98.5 percent) and substituted diketopiperazine (1.5–2.5 percent).

Examples I–III above serve to demonstrate the method of carrying out and the desirable results obtained from the instant invention. By way of comparison, Examples IV and V, following, illustrate hydrolysis with magnesium oxide and cupric oxide leading to undesirable results.

EXAMPLE IV

Magnesium Oxide Hydrolysis

To a stirred 30° C. slurry of 5 g. (approximately 0.017 mole) of crude αAPM (90-95 percent α-L-aspartyl-L-phenylalanine methyl ester, 5–10 percent α-L-aspartyl-L-phenylalanine, 0.5–1.5 percent substituted diketopiperazine) in 94 ml. of distilled water was added portionwise, over 5 minutes, 0.7 g. (0.017 mole) of MgO. The resulting mixture, which had an alkaline pH, was stirred for 3 hours at 30° C. and filtered. Analysis of the cake (2 g.) by TLC showed only substituted diketopiperazine, indicating substantial conversion to this undesirable product. Analysis of the mother liquor by TLC showed α-L-aspartyl-L-phenylalanine, substituted diketopiperazine and no α-APM.

EXAMPLE V

Cupric Oxide Hydrolysis

To a stirred 30° C. slurry of 5 g. (approximately 0.017 mole) of crude α-APM (90–95 percent α-APM, 5–10 percent α-L-aspartyl-L-phenylalanine, 0.5–1.5 percent substituted diketopiperazine) in 34 ml. of water was added portionwise, over 5 minutes, 1.4 g. (0.017 mole) of CuO. The mixture, which had an alkaline pH, was stirred for 3 hours at 30° C. Analysis of the mixture by TLC showed essentially no conversion of α-APM to α-L-aspartyl-L-phenylalanine (α-APM still present).

Although the invention has been described with respect to certain specific embodiments, it is not so limited, and it is to be understood that variations and modifications thereof may be made without departing from the spirit of the invention.

The embodiments of this invention in which an exclusive property or privilege is claimed are defined as follows:

1. A process which comprises contacting, at a reaction pH greater than 7, an alkyl ester of α-L-aspartyl-L-phenylalanine with an aqueous solution containing barium ions to form α-L-aspartyl-L-phenylalanine.

2. A process according to claim 1 wherein the alkyl moiety of said alkyl ester is an alkyl group having from 1 to 3 carbon atoms.

3. A process according to claim 2 wherein the alkyl group is methyl.

4. A process according to claim 1 carried out at a pH greater than about 10.

5. A process according to claim 4 wherein the alkyl moiety of said alkyl ester is an alkyl group having from 1 to 3 carbon atoms.

6. A process according to claim 5 wherein the alkyl group is methyl.

7. A process which comprises contacting, at a reaction pH greater than 7, an alkyl ester of α-L-aspartyl-L-phenylalanine with an aqueous solution containing barium ions, said solution formed using barium, barium hydroxide, or barium oxide, to form α-L-aspartyl-L-phenylalanine.

8. A process according to claim 7 wherein barium hydroxide has been added to the solution.

9. A process according to claim 7 wherein barium oxide has been added to the solution.

10. A process according to claim 7 carried out at a pH greater than about 10.

11. A process according to claim 7 wherein the alkyl moiety of said alkyl ester is an alkyl group containing from 1 to 3 carbon atoms.

12. A process according to claim 11 wherein the alkyl group is methyl.

13. A process which comprises contacting, at a reaction pH greater than 10, a methyl ester of α-L-aspartyl-L-phenylalanine with an aqueous solution containing barium ions, said solution formed using barium hydroxide or barium oxide, to form α-L-aspartyl-L-phenylalanine.

* * * * *